United States Patent [19]
Conway et al.

[11] Patent Number: 6,058,159
[45] Date of Patent: *May 2, 2000

[54] COMPACT SCANNER APPARATUS AND METHOD

[75] Inventors: Granville Todd Conway, Green Village; Michael Patrick Maes, Saddlebrook; Brad Conway, Morristown, all of N.J.

[73] Assignee: Control Screening, L.L.C., Fairfield, N.J.

[*] Notice: This patent is subject to a terminal disclaimer.

[21] Appl. No.: 09/164,986

[22] Filed: Sep. 23, 1998

Related U.S. Application Data

[62] Division of application No. 08/584,469, Jan. 11, 1996.

[51] Int. Cl.⁷ .............................. G21F 5/08; G01F 23/00; B65G 43/00

[52] U.S. Cl. ...................... 378/68; 198/502.1; 198/950; 378/57; 250/359.1; 250/453.11; 250/491.1

[58] Field of Search ............................. 198/502.1, 502.2, 198/840, 841, 950; 250/358.1, 359.1, 453.11, 491.1, 506.1, 519.1; 378/57, 68, 98.2, 98.6, 208, 198

[56] References Cited

U.S. PATENT DOCUMENTS

| | | | |
|---|---|---|---|
| 3,980,899 | 9/1976 | Haas et al. | 250/492 |
| 4,020,346 | 4/1977 | Dennis | 250/358 |
| 4,239,969 | 12/1980 | Haas et al. | 250/359 |
| 4,879,735 | 11/1989 | Owens | 378/57 |
| 5,124,554 | 6/1992 | Fowler et al. | 250/358.1 |
| 5,479,023 | 12/1995 | Bartle | 250/390.04 |
| 5,699,400 | 12/1997 | Lee et al. | 378/57 |

*Primary Examiner*—William E. Terrell
*Assistant Examiner*—Joe Dillon, Jr.
*Attorney, Agent, or Firm*—Ernest D. Buff; Riker, Danzig, Scher Hyland & Perretti LLP

[57] ABSTRACT

A scanner apparatus comprises a tunnel housing having a top, two sides and entrance and exit openings; a bed assembly having a top and side portions wherein the side portions of the bed assembly are substantially fixed to the side portions of the tunnel housing to form a substantially enclosed area; an isolating device located at each of the entrance and the exit of the tunnel housing; a conveyor device for moving an object though the tunnel housing; and an analysis device for analyzing objects within the substantially enclosed area in the tunnel housing. The scanner apparatus has an essentially frameless structure which enhances its capability for scanning tall, wide items.

7 Claims, 9 Drawing Sheets

FIG. 1
(PRIOR ART)

COMPACT SCANNER APPARATUS AND METHOD

CLAIM FOR PRIORITY

This application is a divisional of and claims priority of patent application Ser. No. 08/584,469 which was filed on Jan. 11, 1996 and its subsequent continued prosecution application having the same number filed on Jul. 17, 1998. The continued prosecution application was co-pending at the time of the filing of the divisional. The inventors are the same. No new matter has been introduced.

FIELD OF THE INVENTION

The present invention relates to the field of relatively compact scanner apparatus and methods and more particularly to apparatus and methods for scanning objects which are transported by a conveyor belt through a temporarily sealed tunnel, such as in contraband detection systems.

BACKGROUND OF THE INVENTION

Scanners, particularly "compact" scanners, are used for detecting contraband at schools, correctional mail screening, courthouse security, airport hand parcels, and industrial processing applications. These scanners employ tunnel housing, an isolating device, a conveyor device, a bed assembly housing in which the conveyor device is substantially located, and framing. The tunnel housing typically has a top portion, and side portions which together with a top portion from the bed assembly housing, form a substantially enclosed area. The tunnel housing is also provided with entrance and exit openings to the substantially enclosed area.

The isolating device substantially covers the entrance and exit openings and is typically in the form of two separate lead curtains. One lead preferably fabric curtain is bolted to flat framing at the entrance opening, and the other lead preferably curtain is bolted to flat framing located at the exit opening. Isolating devices permit the passage of conveyed objects into the substantially enclosed area of formed by the tunnel housing and the top portion of the bed assembly housing, which is typically X-ray scatter lead shielded, and may also substantially exclude light, noise, heat, cold, moisture, dryness, electrostatic or electromagnetic fields, dust gasses or chemical vapors while the conveyed objects are being analyzed.

Scanners analyze objects which are brought into the enclosed area of formed by the tunnel housing and the top portion of the bed assembly housing by the conveyor device. The conveyor devices are typically comprised of relatively short lengthed conveyor belts. Short lengthed conveyor belts, particularly those with a relatively low length to width ratio, such as of less than twelve to one, 12 to 1, often mistrack causing damage to the conveyor belts, objects being scanned, and other parts of the system. Currently, expensive and elaborate tracking mechanisms such as precise construction of components, toothed or perforated belting to mesh with drive gears or belt grooves, raised profile rails, servo-drive tracking adjustment mechanisms, and reliance on a human attendant are used for tracking conveyor belts.

The framing provided to structurally connect the tunnel housing, the bed assembly housing, the conveyor device and the isolating device is often elaborate, wasteful, and space consuming. Scanners are needed which are more compact in overall width and length without sacrificing the width of the enclosed area inside the tunnel housing.

SUMMARY OF THE INVENTION

A compact and reliable scanning apparatus and method is provided. The scanner in one embodiment comprises a conveyor device, a tunnel housing, a bed assembly housing, an isolating device, and one or more analysis devices. The tunnel housing is comprised of top and side portions which together with a top portion from the bed assembly housing form a substantially enclosed area for analyzing objects. The bed assembly housing encloses most of the components of the conveyor device.

The conveyor device is typically comprised of a conveyor belt, rollers and a conveyor tracking device. The conveyor tracking device is comprised of first and second channels formed in first and second rails. The conveyor belt, preferably includes a first edge and a second edge, and an inner surface and an outer surface. The first and second edges of the conveyor belt typically pass through the first and second channels formed in the first and second rails, respectively. The first and second rails inhibit the conveyor belt from misaligning. The conveyor belt preferably traverses a forward path and a return path and the first and second rails are preferably provided in the return path. The first and second rails are preferably opposite one another.

The isolating device is preferably comprised of separate first and second curtains which extend outward from separate first and second rods, respectively. The first and second rods and curtains are preferably adaptable for insertion into first and second slots, respectively, located in the top portion of the tunnel housing, near the entrance and exit openings, respectively. The slots can also be called slits. The rods, the curtains, and the slots of the housing, are typically adaptable so that the curtains can be inserted into and through the appropriate slot but the rods cannot be inserted through the appropriate slot. After the rods and curtains have been inserted into their respective slot each curtain should entirely the cover either the exit or the entrance opening. The isolating device preferably temporarily seals off the substantially enclosed area bounded by the tunnel housing and the top portion of the bed assembly housing so that no X-rays will leak out.

In one embodiment of the present invention the tunnel housing, the bed assembly housing, the conveyor device, the one or more analysis devices, and the isolating device are constructed in a manner which provides a largely frameless scanner apparatus. The bed assembly housing preferably comprises a top portion which is used as with the tunnel housing to form a substantially enclosed area. The bed assembly housing further preferably comprises first and second side portions which are preferably fixed to the first and second side portions of the tunnel housing providing structural support and reducing the need for framing. One of the analysis devices may be comprised of a substantially steel member which is used to further connect the tunnel housing with the bed assembly housing. The analysis devices may be various types including X-ray or electromagnetic generators and detectors and optimal vapour detectors.

The efficient construction of the conveyor device, the isolating device, the tunnel housing, the bed assembly housing, and the one or more analysis devices of the scanner maximizes the cross sectional area, and the width and height for the enclosed area of formed by tunnel housing and the top portion of the bed assembly housing of the scanner for a given overall cross sectional width and height.

BRIEF DESCRIPTION OF THE DRAWINGS

FIG. 1 is a frontal view of a prior art framed tunnel;

DETAILED DESCRIPTION OF THE DRAWINGS

Prior Art

Figure 1:
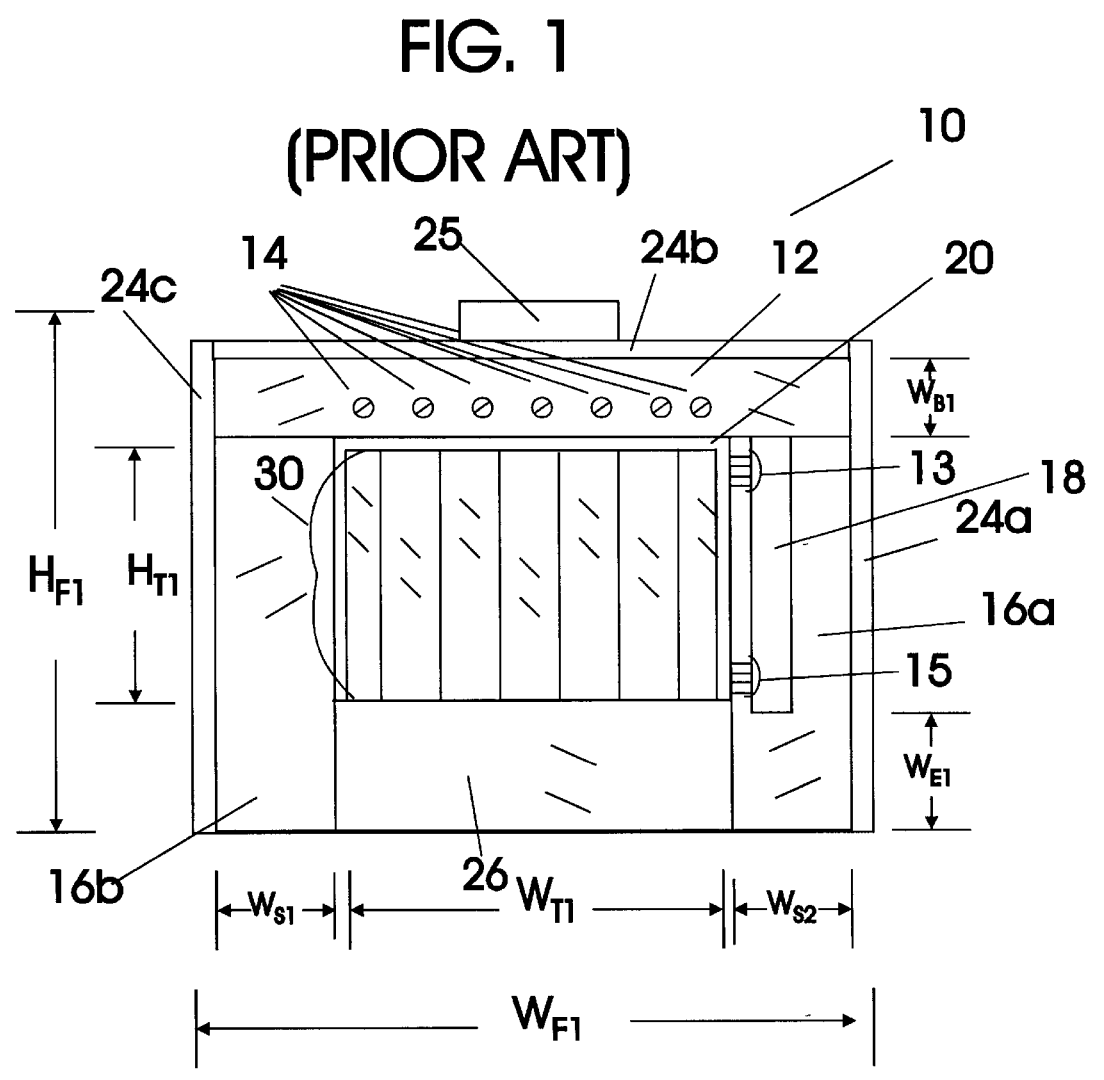
Figure 2:
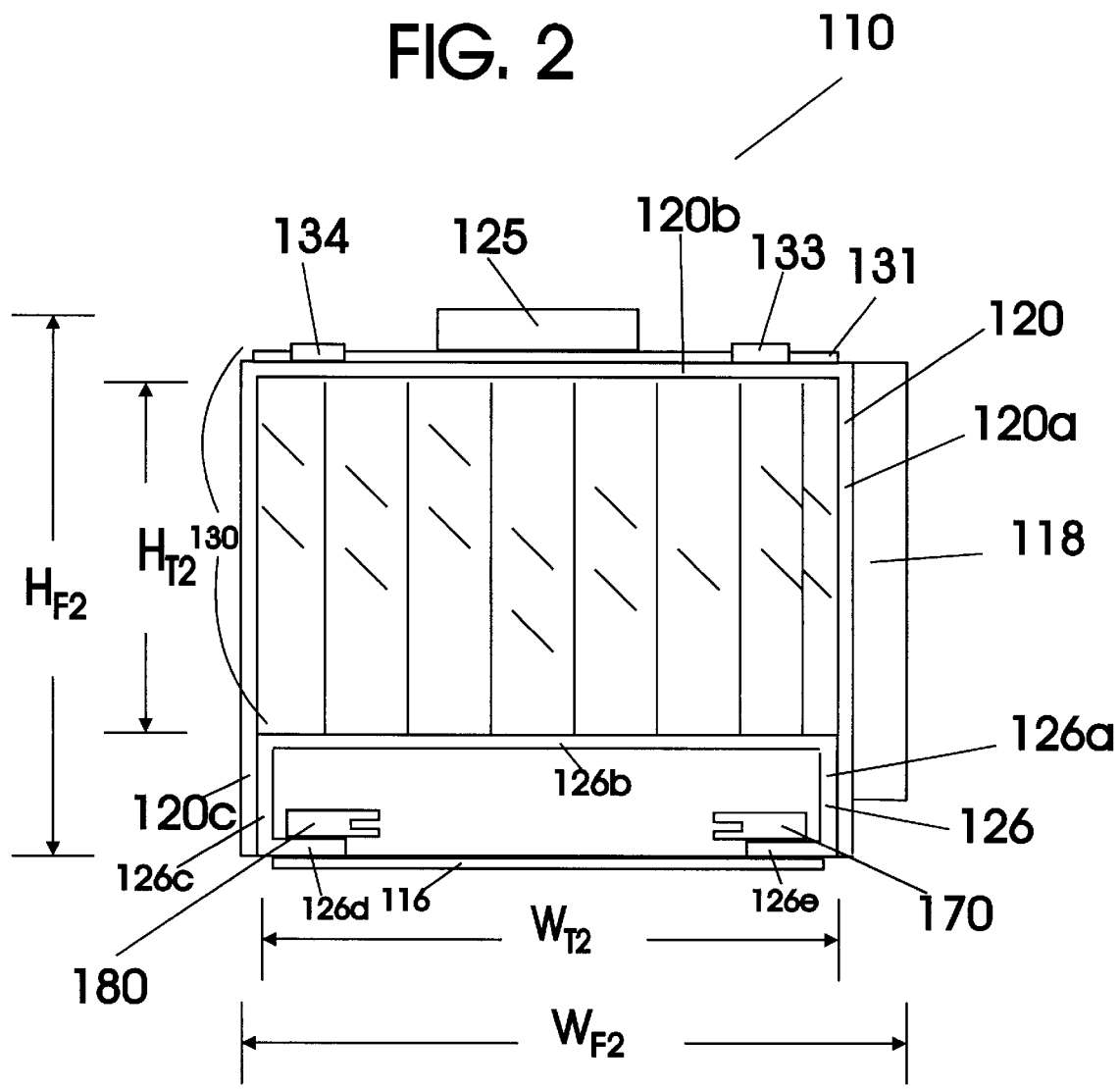
FIG. 2 is a frontal view of a scanner embodiment of the present invention for convenience shown without its rollers or a conveyor belt.

A frontal view of a scanner 10 known in the prior art is shown in FIG. 1. The scanner 10 includes top framing 12, bolts 14, side framing 16a and 16b, detector tray assembly 18, tunnel housing 20, bed assembly housing 26, cosmetic panels 24a, 24b, and 24c, detector/generator 25 and isolating device portion 30.

The prior art scanner 10 has an overall height $H_{F1}$, and an overall width of $W_{F1}$. The area enclosed by the tunnel housing 20 and a top of the bed assembly housing 26 and covered by the isolating device portion 30 has a height of $H_{T1}$ and a width of $W_{T1}$. The tunnel housing 20 is usually leadlined on the outside. The side framing 16a and 16b ties or connects together the tunnel housing 20 and the bed assembly housing 26. The bed assembly housing 26 includes the motor, rollers, and the conveyor belt, for carrying items to be scanned, all of which are not shown. The scanner 10 of the prior art typically does not include a tracking mechanism to prevent the conveyor belt from misaligning. The top framing 12 ties the side framing 16a and 16b together and holds a heavy X-ray curtain bar, not shown, by use of bolts 14.

In order to allow the scanner 10 to be compact enough to fit through doors so that it can be transported and to consume less hallspace which can be scarce or expensive, there are limitations on the overall height $H_{F1}$ and the overall width $W_{F1}$ of the scanner 10. However, the top framing 12 also has to have a sufficient width $W_{B1}$ to allow mounting of the isolating device portion 30 and to provide structural support for the scanner 10. Similarly, side framing 16a and 16b have to have sufficient thickness to provide structural support for the scanner 10.

The frontal view of the scanner 10 in FIG. 1 shows only entrance framing into the enclosed area or tunnel bounded by tunnel housing 20 and the top of the bed assembly housing. However, the exit framing would be similar. Lengthwise framing would also be used (not shown) to connect the side framing 16a and 16b at the entrance with its counterpart side framing at the exit of the tunnel housing 20.

The tunnel housing 20 typically supports at least the weight of a Cathode Ray Tube ("CRT") and either a heavy generator and lead housing or a leaded steel detector tray (not shown). A detector/generator 25 is shown in FIG. 1. The heavy framing supports the tunnel housing 20 and outside lead and spaces out and supports cosmetic panels 24a and 24c and top panel 24b, which often extend down well below the bed assembly 26 to casters, not shown. The prior art of smaller scanners are constructed in this heavily framed method, except that the framing often is separated below the bed assembly housing 26 to allow placement of the scanner apparatus 10 on either a table or a framed cart. In order to roll these compact scanners through narrow doorways, or to station them in narrow hallways, the available square tunnel space inside the area bounded by the tunnel housing 20 and the top of the bed assembly housing 26 left after designing in heavy framing becomes too tight for many screened items, necessitating a still larger machine, or a slow and invasive individual visual parcel inspection by hand.

The detector tray assembly 18 is not used as a structural support for the tunnel housing 20 but rather is hung on the tunnel housing 20 such as by connectors 13 and 15.

DESCRIPTION OF THE EMBODIMENTS OF THE INVENTION

Figure 3:
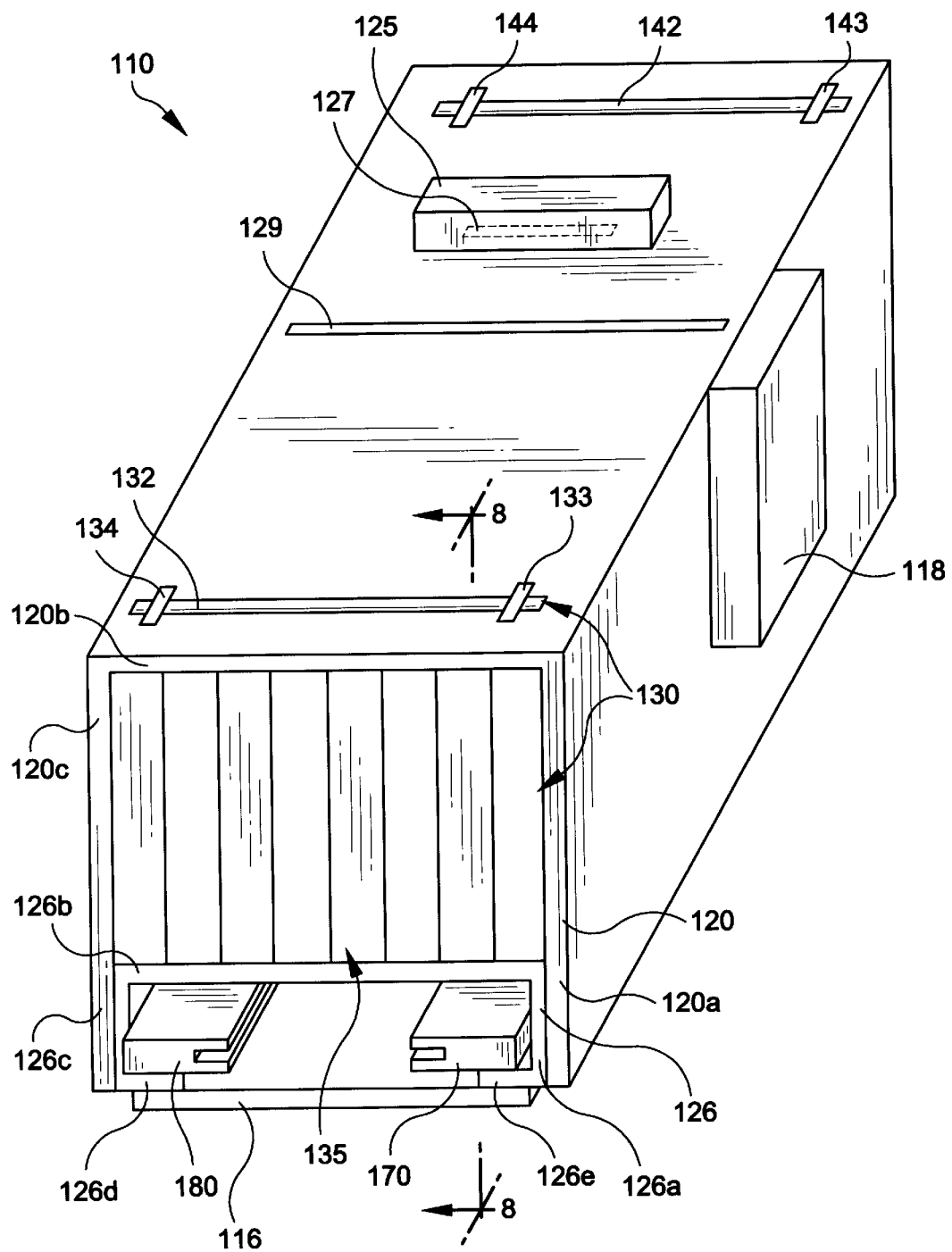
FIG. 3 is a perspective view of the outside of one embodiment of the scanner apparatus and method of the present invention for convenience shown without its rollers or its conveyor belt.
Figure 4:
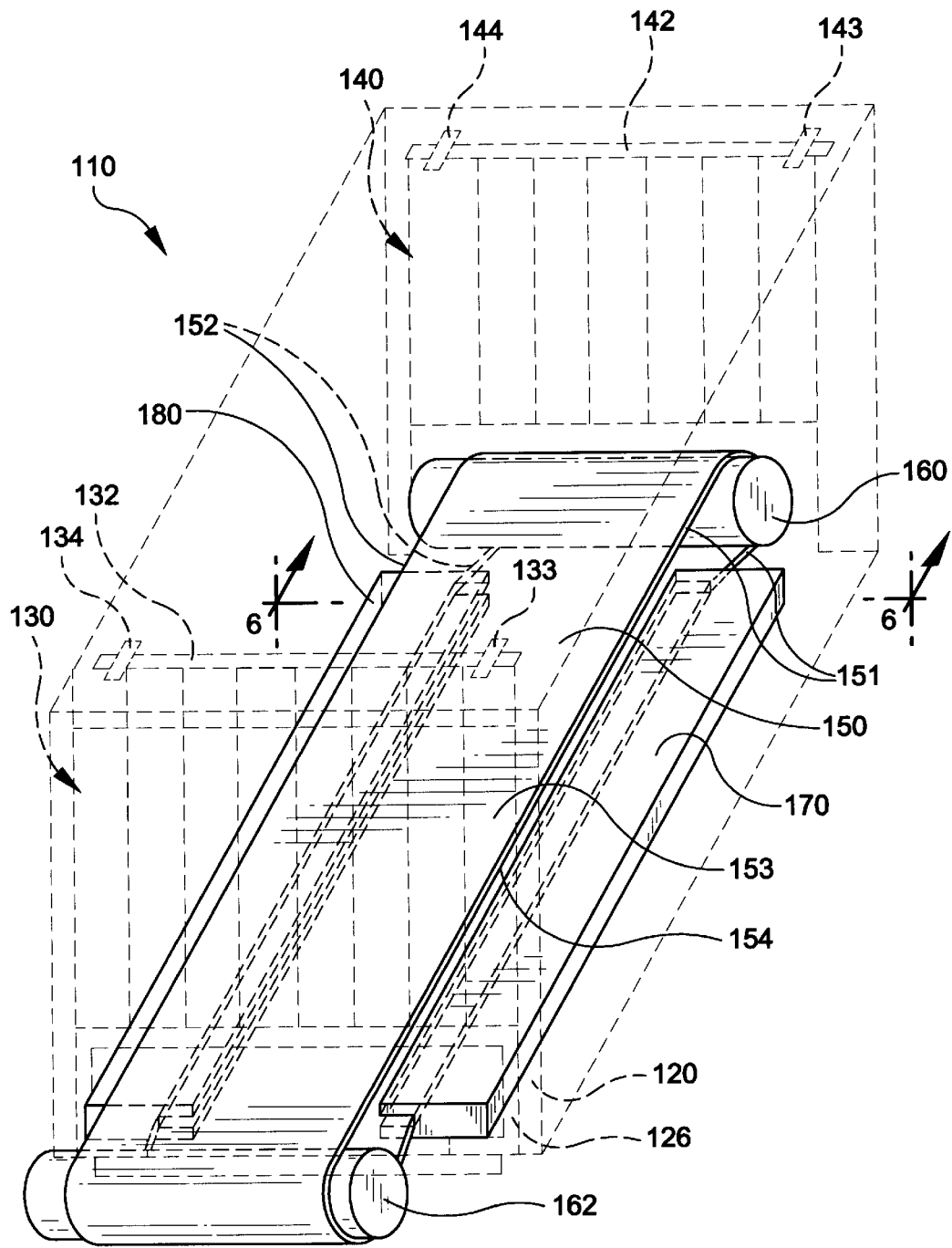
FIG. 4 is a perspective view of the innards of the embodiment of FIG. 3, shown with its rollers and its conveyor belt.

FIG. 2 shows a frontal view of a scanner apparatus 110 in accordance with an embodiment of the present invention. FIG. 2 shows the scanner apparatus 110 without a conveyor belt 150 or rollers 160 and 162 as is shown in FIG. 4, to more easily show aspects of this embodiment. The view in FIG. 2 shows a bottom plate 116, detector assembly 118, tunnel housing 120, bed assembly housing 126, isolating device portion 130, and guide rails 170 and 180. FIG. 3 shows an outside perspective view of the scanner apparatus 110, again without the rollers 160 and 162 and without the conveyor belt 150, for convenience of illustration.

The view of FIG. 3 additionally illustrates vapour detector 125, slot 127, and X-ray slot 129. The detector assembly 118, vapour detector 125, slot 127, and X-ray slot 129 comprise parts of one or more analysis devices. The slot 127 allows vapours to be sensed by the vapour detector 125. The X-ray slot 129 would in practice be covered by either a generator and collimator housing or detector housing which is not shown, such as an electromagnetic detector or generator. If generator, it would be covered by a steel bonnet (not shown), and a detector housing (not shown) would be located below the bed assembly housing 126.

Parts of isolating device portions 130 and 140 are also shown in FIG. 3. FIG. 4 shows an inside perspective view of the scanner apparatus 110 with the rollers 162 and 160 and conveyor belt 150, but without some of the outside components shown in FIG. 3.

The scanner apparatus 110 shown in FIG. 2 has an overall height of $H_{F2}$ and an overall width of $W_{F2}$, which are may be the same as $H_{F1}$ and $W_{F1}$ shown in the prior art device of FIG. 1. However, the height $H_{T2}$ and the width $W_{T2}$ for the enclosed area bounded by the tunnel housing 120 and a top portion 126b of the bed assembly housing 126 is considerably greater than the area bounded by the tunnel housing 20 and the top of the bed assembly housing 26 of FIG. 1 of the prior art, i.e. $H_{T2}$ is greater than $H_{T1}$, and $W_{T2}$ is greater than $W_{T1}$. Many aspects of embodiments of the present invention combine to make this increased enclosed tunnel area possible without increasing the overall size of the scanner apparatus 110 from the prior art scanner 10 of FIG. 1.

Among these aspects are the manner of forming and connecting isolating device portions 130 and 140, the compact tracking device comprised of the guide rails 170 and 180, the use of a detector assembly 118 comprised of steel and lead, and connected on one side of the tunnel housing 120, and the reduction of unnecessary framing to provide an essentially frameless construction. These aspects of embodiments of the present invention and other aspects, provide other benefits which will be described further herein.

The reduction of unnecessary framing is an important aspect of the present invention. Instead of using framing as in FIG. 1, the tunnel housing 120 is thickened to around 0.125 inches. The preferably one piece tunnel housing is comprised of side portions 120a and 120c, and a top portion 120b. The tunnel housing 120 may be thicker or thinner depending on the scanner size. The side portions 120a and 120c of the tunnel housing 120 are preferably extended down to the bottom of the bed assembly housing 126. The bed assembly housing 126 is comprised of side portions 126a and 126c, top portion 126b, and bottom portions 126d and 126e. The side portions 120a and 120c are then structurally joined, by bolts or otherwise, to side portions 126a and 126c respectively of the bed assembly housing 126. The top portion 126b of the bed assembly 126 preferably provides the bottom or base to the substantially enclosed area bounded by the tunnel housing and the bottom portion 126b.

In this embodiment the bed assembly housing 126 functions as a beam over the enclosed tunnel length and closes the scanner apparatus 110 into a stronger box construction. Lead shielding is provided on the inside of the tunnel housing 120, unlike the outside as in the prior art. The outside of the tunnel housing 120 can then be painted so that cosmetic panels or frames are not needed. Bolting the tunnel housing 120 to the bed assembly housing 126 also clamps the lead shielding on the inside of side portions 120a and 120c of the tunnel housing 120 firmly at the bottom. Retainers, not shown, may be used to hold the lead under the top portion 120b of the tunnel housing 120. Lead on the inside sides of the tunnel housing 120 can additionally be held by glue, additional retainers or hardware. Low friction tape or the retainers protect any items from the lead shielding, which can also be painted.

The detector assembly 118 is preferably one leaded piece of steel which carries one full detector array, the other generally being at right angles above or below the tunnel, but it is preferred that the detector assembly 118 also structurally join the tunnel housing 120 and the bed assembly housing 126 around a slit opening, not shown, through which X-rays pass to the detectors. This detector assembly 118 is also preferably cosmetically finished outside to dispense with the bulkiness, cost and maintenance for framed outside cosmetic panels which were required by the prior art. The detector assembly 118 is only on one side, and its width is preferably much narrower than the width $W_{S2}$ of the prior art side framing shown in FIG. 1. Typically the detector assembly 118 can be about one-third, ⅓, the width of the prior side framing $W_{S2}$. Since the prior art required two side framing members, this is a substantial space savings, which may equal for example, at least five additional inches available for the width $W_{T2}$, of the tunnel housing 120. The width, $W_{T2}$ is the key dimension allowing larger items to be screened, the length of an item which can travel along a conveyor belt such as a belt 150, is practically unlimited for a conveyorized scanner. The top of the tunnel also needs no framing, in part due to the isolating device portion 130 discussed herein which takes up a very low height, which may be a fifth of the width $W_{B1}$ of the top framing of the prior art. In this manner tunnel height $H_{T2}$ can be increased to 2 or 3 inches more.

Figure 8:
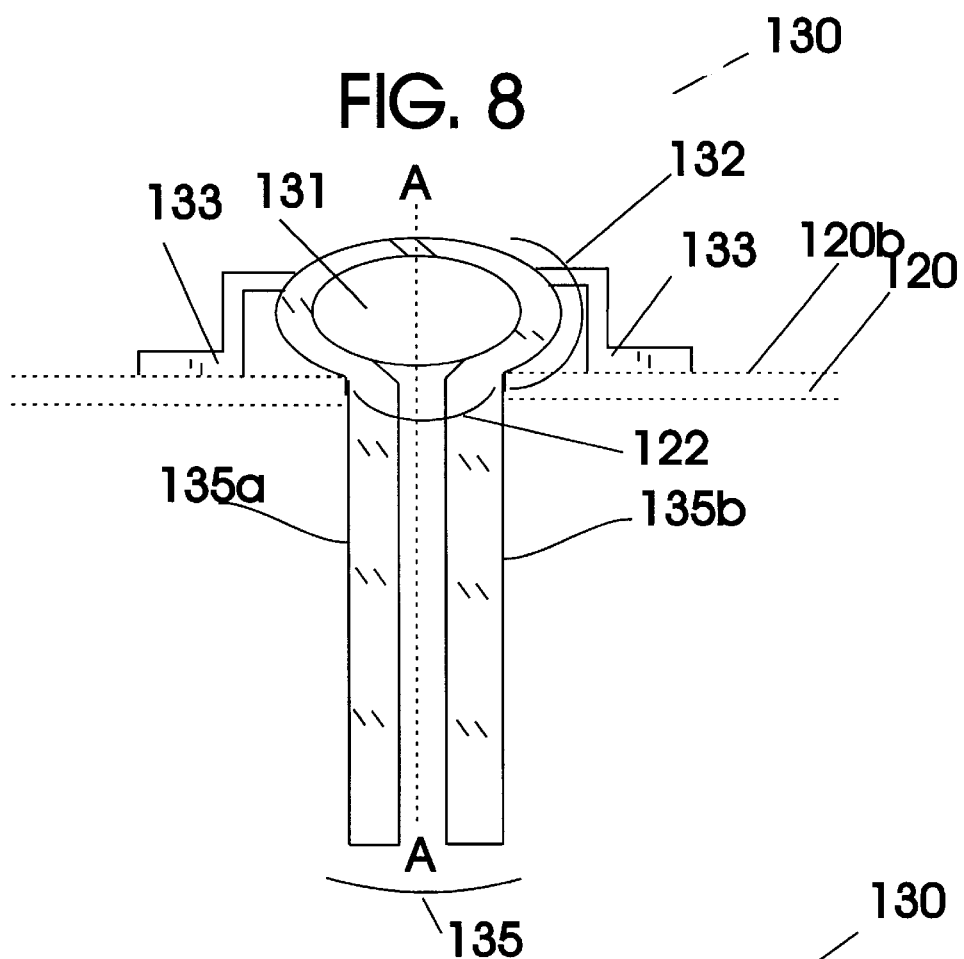
FIG. 8 is a side cross sectional view of a curtain used as part of an isolating device for use with the conveyor device of the embodiment of FIG. 4.
Figure 9:
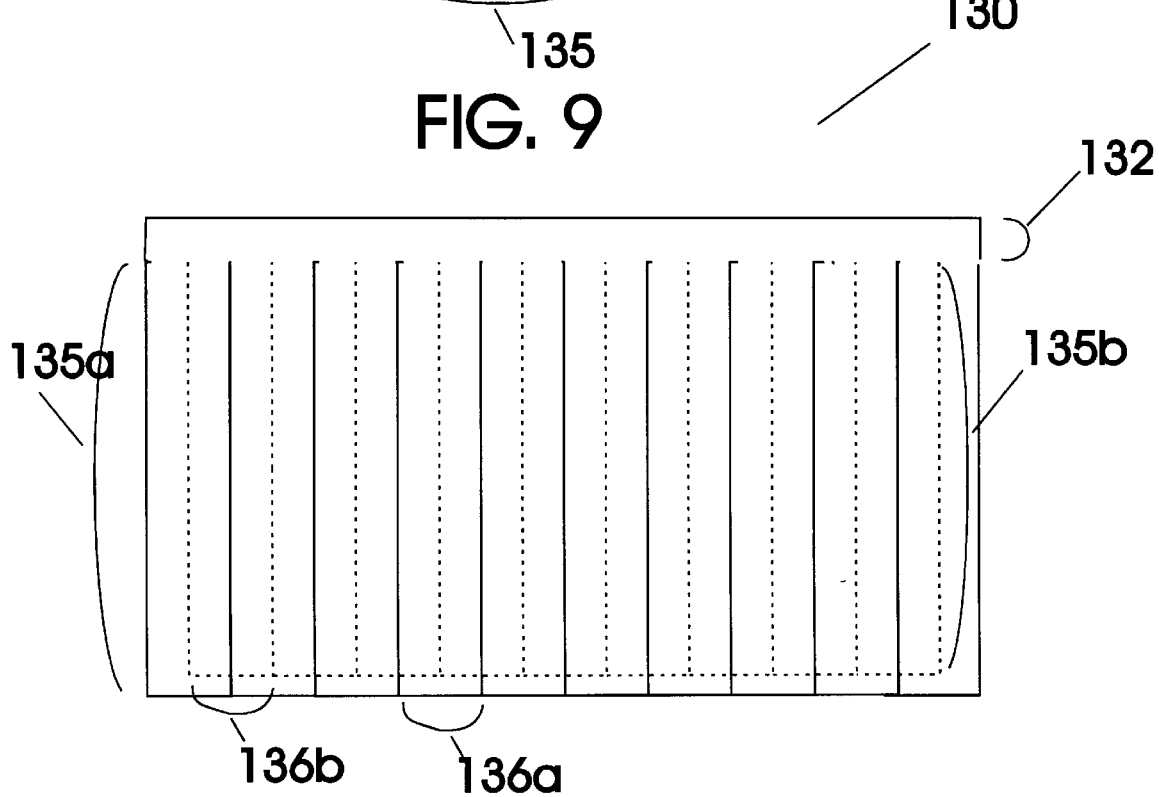
FIG. 9 is a front view of an overlapping configuration for an curtain used as part of an isolating device.

FIGS. 2, 3, 4, 8, and 9 will be used to describe the isolating device portions 130 and 140. FIGS. 8 and 9 show cross sectional and frontal views of the isolating device portion 130. FIG. 8 is a cross sectional view of FIG. 3 taken along line AA. FIG. 9 is a view of the isolating device portion 130 prior to insertion into a slot 122 of the top portion 120b of the tunnel housing 120. Isolating device portions 130 and 140 are preferably substantially the same and therefore only isolating device portion 130 is illustrated in detail in FIGS. 8 and 9.

As shown in FIGS. 3 and 4, isolating device portions 130 and 140 are located at the entrance openings and exit openings, respectively, of the scanner apparatus 110. The isolating device portions 130 and 140 include rods 131 and 141, rounded curtain portions 132 and 142, and flat curtain portions 135 and 145, respectively, as shown for isolating device portion 130 in the cross sectional view of FIG. 8. The rod 131 and the rounded curtain portion 132 of the isolating device portion 130 is mounted to the top portion 120b of the tunnel housing 120 of the scanner apparatus 110 by mounting pieces 133 and 134 as shown in FIGS. 3 and 8. The mounting pieces 133 and 134 may be clamp like instruments. Similarly the rod 141 and the rounded curtain portion 142 of the isolating device portion 140 is mounted to the top portion 120b of the tunnel housing 120 of the scanner apparatus 110 by mounting pieces 143 and 144 as shown in FIG. 3 and is substantially similar to FIG. 8.

The flat curtain portion 135, the rounded curtain portion 132, and the rod 131 are preferably constructed together and then inserted through a slot 122 in the top portion 120b of the tunnel housing 120 as shown by FIGS. 3 and 8. The rod 131 and the rounded curtain portion 132 are then preferably mounted to the tunnel housing 120 by mounting pieces 133 and 134 so that there is a tight seal and the slot 122 is completely covered by the rod 131, rounded curtain portion 132, and the flat curtain portion 135.

The flat curtain portion 135 is preferably comprised of a front section 135a and a rear section 135b. The front section 135a is preferably cut into flaps of material 136a, as shown in FIG. 9. The rear section 135b is preferably cut into flaps of material 136b, as shown by the dashed lines in FIG. 9. The flaps of material 136a and 136b preferably overlap as shown in FIG. 9. The curtain is typically made of lead filled vinyl/fabric laminate. The rods 131 and 141 can be steel, aluminum, wood, or any material that holds the curtain in place.

The tunnel housing 120 and the isolating device portions 130 and 140 generally provide a completely enclosed area inside the scanner apparatus 110. However, it is not necessary, and in fact may be desirable that portions of the conveyor belt 150 lie outside the enclosed area. In addition, the bed assembly housing 126, although not shown outside the enclosed area, may as known in the art be provided outside the enclosed area. In fact, the FIG. 4 illustration shows the roller 162 and a portion of the conveyor belt 150 outside the enclosed area. The roller 160 may also be outside the enclosed area.

The enclosed area makes the scanner apparatus 110 particularly useful as a security or screening device, where electromagnetic radiation or X-rays are used and it is desirable to have such radiation or X-rays contained. An appended section of plastic housing can be added in front of the isolating device portion 130 and the conveyor belt can be extended further and into the extra plastic housing. This extra plastic housing can be used to prevent an individual from putting his hands into the enclosed area beyond the isolating device portion 130 and inside the tunnel housing 120. The use of a slot 122 for the isolating device portion 130 in the top portion 120b of the tunnel housing 120 allows for the easy attachment of such an extra plastic housing, prior in position, to the isolating device 130. I.e. the extra plastic housing can be attached in front of the isolating device portion 130.

Figure 5:
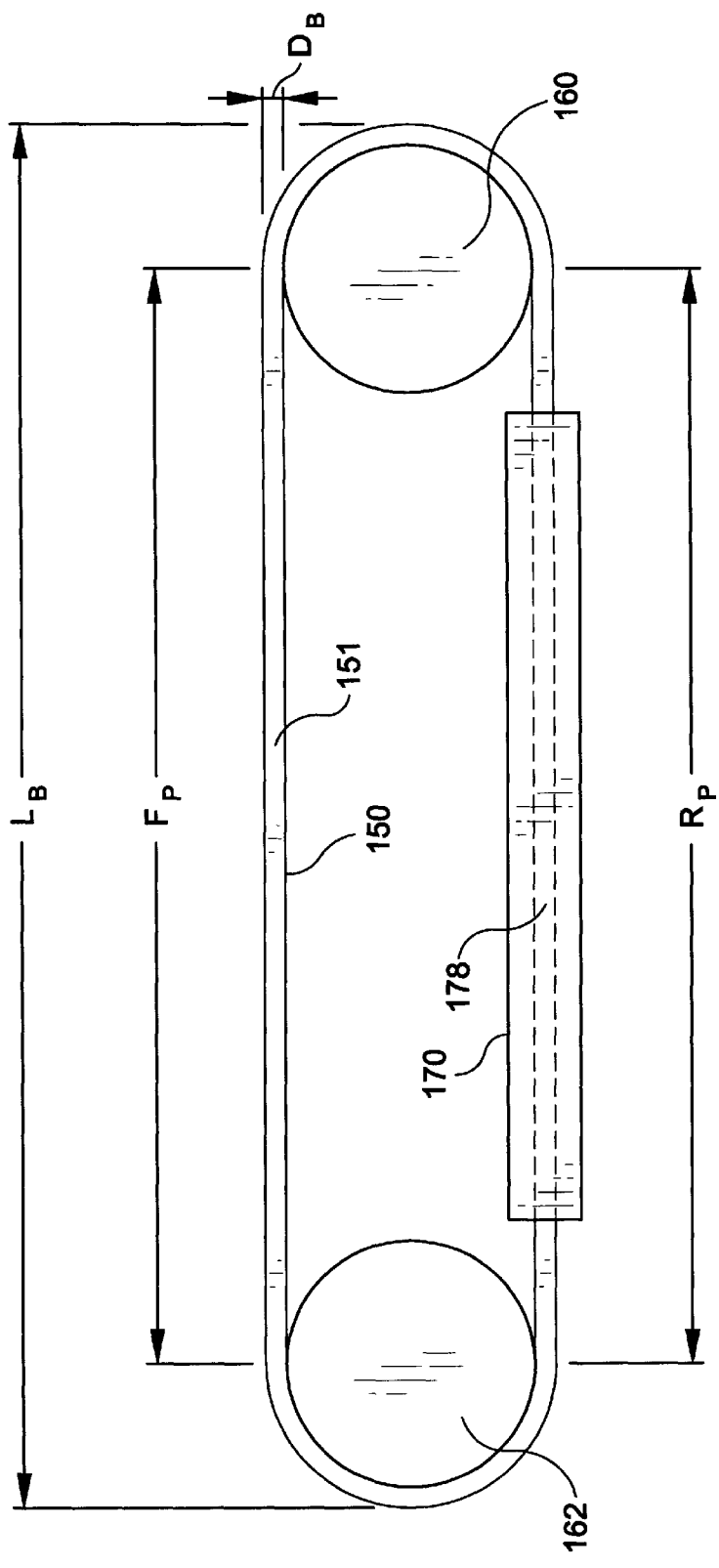
FIG. 5 is a side view of a conveyor belt and tracking device for use with the embodiment of FIG. 4.
Figure 6:
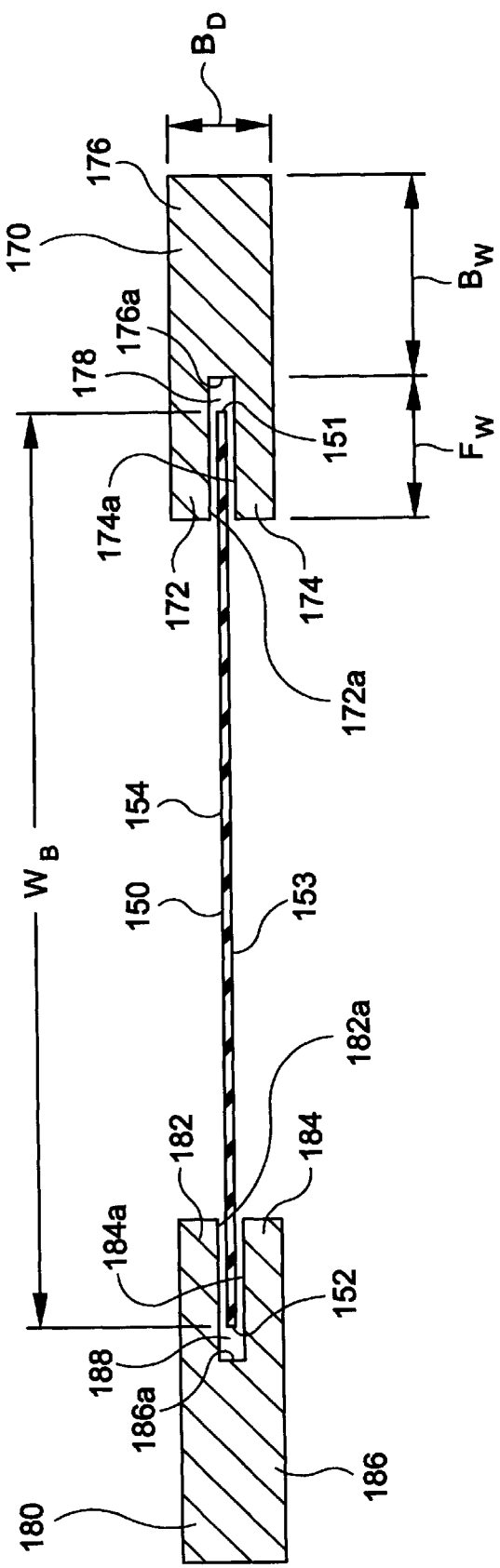
FIG. 6 is a cross sectional view of the tracking device and the portion of the conveyor belt in the return path of the embodiment of FIG. 4.
Figure 7:
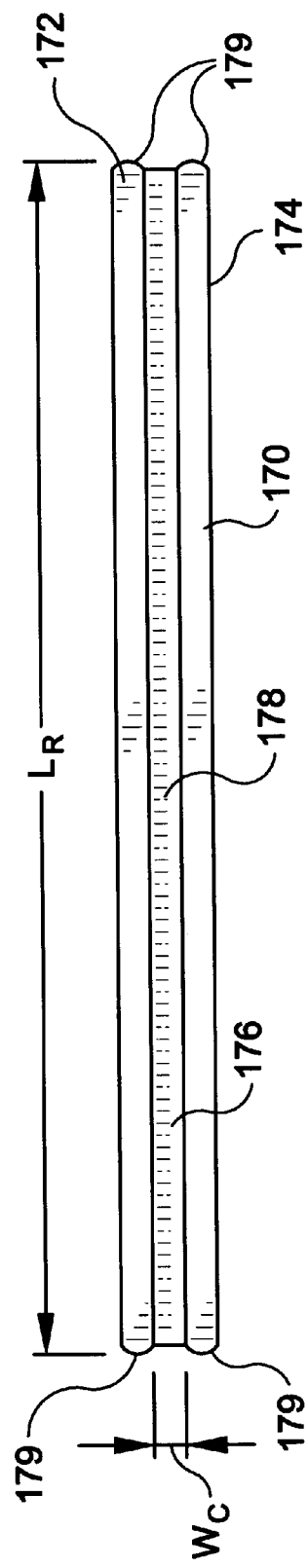
FIG. 7 is a side view of one of the rails for use in the tracking device in the embodiment of FIG. 4.

The inside of scanner apparatus 110 will be described with reference to FIGS. 2, 4, 5, 6, and 7. FIG. 4 is a perspective view of the scanner apparatus 110 with the tunnel housing 120, bed assembly housing 126 and isolating device portions 130 and 140 shown in dashed lines. FIG. 5 is a side view of the conveyor belt 150 and a moving device comprising rollers 160 and 162. FIG. 6 is a cross sectional view of guide rails 170 and 180 and conveyor belt 150, taken along line BB in FIG. 4. FIG. 7 is a frontal view, looking into a channel 178 of the guide rail 170.

The conveyor belt 150, as shown in FIGS. 4, 5, and 6 is typically a belt formed substantially in the shape of a loop. The conveyor belt 150 may be a woven carcass type belt with elastomer covering. The conveyor belt 150 is comprised of a first edge 151, a second edge 152, an outer surface 153, and an inner surface 154, shown in FIGS. 4 and 6. The first edge 151 and the second edge 152 are shown as darkened dashed lines for the portion of the conveyor belt 150 which is in the return path in FIG. 4. The first and second edges 151 and 152 pass through channels 178 and 188 of guide rails 170 and 180, respectively, during the movement or rotation of the conveyor belt 150, as shown in FIGS. 4 and 6. The conveyor belt 150 traverses a forward path, "$F_P$", and a return path, "$R_P$", as shown in FIG. 5. The forward path and the return path may be relatively short, such as for example forty-three inches long each. The conveyor belt has a length "$L_B$" shown in FIG. 5, and a width, "$W_B$", shown in FIG. 6, when it is fully extended over the rollers 160 and 162. The length/width ratio of the conveyor belt 150, or $L_B/W_B$, is preferably less than twelve to one. The length to width ratio can for example be as low as two or three to one or lower. The length $L_B$ may be 47 (forty-seven) inches while the width $W_B$ may be 15.75 inches.

The guide rails 170 and 180, are comprised of inner flanges 172 and 182, outer flanges 174 and 184, and border pieces 176 and 186, respectively. The guide rails 170 and 180 preferably lie entirely between the rollers 160 and 162 as shown in FIG. 4. The inner flange, outer flange, and border piece of each guide rail are preferably constructed as one unit from the same material, but may be constructed in other manners. The material may be a wide variety of materials such as wood, fiberglass, aluminum, steel, nylon, Polypropylene (P.P.), Polyethylene (P.E.), or High Density Polyethylene (H.D.P.E.). The border pieces 176 and 186 are preferably rectangular units having a length, width, and a depth, where the length is greater than the width, and the width is greater than the depth. For example, border piece 176 of guide rail 170 preferably has a length of $L_R$, a width of $B_W$, and a depth of $B_D$ as shown in FIGS. 6 and 7. Dimensions of 30.25 inches for the length, two inches for the width, and 0.125 inches for the depth can be used. These dimensions allow the guide rail 70 to be mounted firmly to part of bed assembly housing 121 as shown in FIG. 2, but also to be compact so that the guide rail 170 does not affect other operations or take up too much of the available space for the enclosed tunnel area of the scanner apparatus 110. These dimensions may vary for the length.

The guide rails 170 and 180 are typically rounded off at their edges to allow for a smooth transition and to prevent damage to the belt. For example, guide rail 170 as shown in FIG. 7, has four rounded edges 179, at its two ends.

The width of the channel 178 is shown in FIG. 7 as $W_C$, and is preferably slightly greater than the depth of the conveyor belt, $D^B$, which is shown in FIG. 5. For a typical X-ray scanner, the width of the channel may be about 0.19 inches while the depth of the conveyor belt may be about 0.125 inches, and proportionally larger for a thicker conveyor belt. The width of the channel 188 preferably has similar dimensions. These dimensions for the channels 178 and 188 provide an appropriate amount of clearance and control of the conveyor belt 150. The inner flanges and outer flanges preferably overlap the conveyor belt 150 by a length of $F_W$, which may be 0.625 inches, minus the clearance between the edge 151 of the conveyor belt and the surface 176a of the border piece 176, which clearance may be ⅛ (one-eighth) of an inch. This overlap length provides an appropriate amount of control to prevent the conveyor belt 150 from buckling.

The rollers 160 and 162 are preferably rotatably mounted to the tunnel housing 120 and/or bed assembly housing 126 by bearings in a manner known to those skilled in the art.

In operation, a person inserts an object, such as a purse, through the flat curtain portion 135 of the isolating device portion 130. The flat curtain portion 135 is preferably made of a flexible material and is typically not mounted to the top portion of the bed assembly housing 126b, so that an object can be inserted. The object is placed on the conveyor belt 150 and passes through the isolating device portion 130. The conveyor belt 150 can be caused to rotate or move by any manner known in the art. The object is transported by the conveyor belt 150 to the exit of the scanner apparatus 110, and past the isolating device portion 140.

During the movement of the conveyor belt 150 the inner flange 172 has a surface 172a which is substantially parallel and substantially adjacent to a portion of the inner surface 154 of the conveyor belt 150 as shown in FIG. 6. The outer flange 174 has a surface 174a which is substantially parallel and substantially adjacent to a portion of the outer surface 153 of the conveyor belt 150 as also shown in FIG. 6. The border piece 176 has a surface 176a which during the movement of the conveyor belt 150 is substantially parallel to a part of the first edge 151 of the conveyor belt 150. In normal operation, the first edge 151 is preferably about ⅛ (one-eighth) of an inch from the surface 176a. The second edge 152 is preferably a similar distance form the surface 186a in normal operation. This allows for a certain amount of clearance. The inner flange 182, outer flange 184, and border piece 186 have similar surfaces 182a, 184a, and 186a. A portion of the inner surface 154 of the conveyor belt 150 which at one time is in the channel 178, eventually comes in contact with the rollers 160 and 162. Similarly a portion of the inner surface 154 of the conveyor belt 150 which at one time is in the channel 88, eventually comes in contact with the rollers 160 and 162.

During the movement of the conveyor belt 150, due to the low length to width ratio, the first and second edges, 151 and 152 respectively, of the conveyor belt 150 may drift. For example, the first edge 151 may drift far enough to come in contact with the surface 176a of the border piece 176. When this drifting occurs, the conveyor belt is prevented from becoming further misaligned by the inner flange 172, outer flange 174, and the border piece 176. The border piece 176 prevents the conveyor belt 150 from drifting further. The inner flange 172 and outer flange 174 prevent the conveyor belt 150 from bending substantially after the first edge 151 contacts the surface 176a of the border piece 176. The inner flange 182, outer flange 184, and border piece 186 preferably provide the same function when the second edge 152 of the conveyor belt 150 drifts towards the border piece 186.

Figure 10:
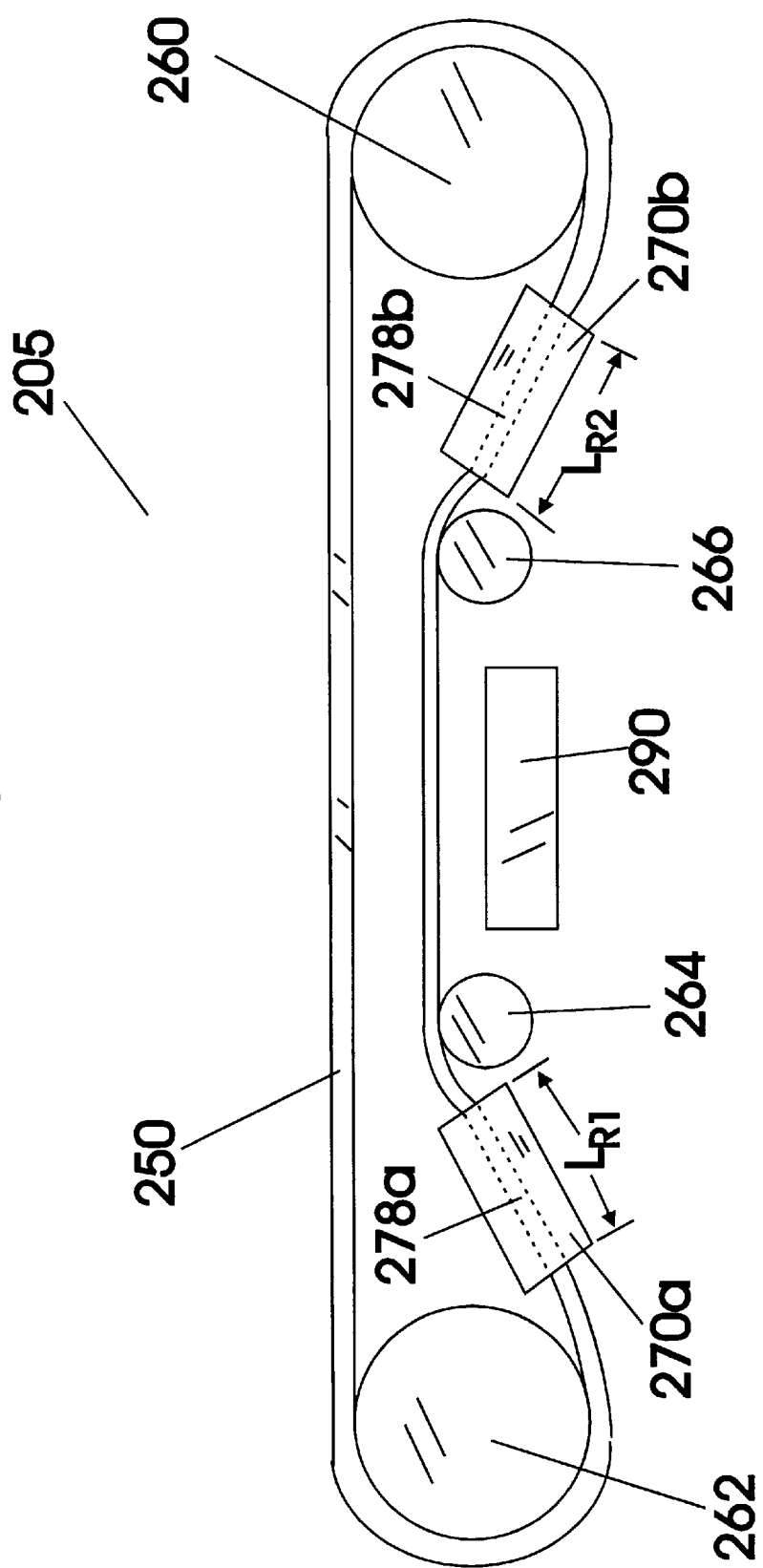
FIG. 10 is a side view of another embodiment for a conveyor belt and tracking device in accordance with the present invention.

FIG. 10 is a side view of another embodiment for a tracking device 205 preferably for use with a scanner apparatus similar to scanner apparatus 110 in accordance with the present invention. Tracking device 205 includes conveyor belt 250, preferably motorized rollers 260 and 262, idle rollers 264 and 266, and guide rails 270a and 270b. Also shown is an obstacle 290, around which the conveyor belt 250 winds. In the tracking device 205 the guide rails 270a and 270b are preferably about five inches in length $L_{R1}$ and $L_{R2}$. There are also preferably guide rails 280a and 280b, which are not shown, but which are located on the other side of conveyor belt 250, which are preferably mirror images of guide rails 270a and 270b. The guide rails 280a and 280b serve a similar function to the guide rail 180 in FIG. 3. The guide rails 270a, 270b, 280a, and 280b are preferably mounted on inclined brackets.

The present invention in its various embodiments solves many problems of the prior art dealing with scanner apparatus and methods. However, those skilled in the art will recognize that various aspects of the present invention can be put to uses other than in scanning apparatus and methods.

The improved tracking aspect provides an economical means of automatic, mechanical conveyor belt tracking, preferably using a standard specification belt. The improved isolating aspect of embodiments of the present invention provides an improved means of fitting an isolation curtain to a housing, in a manner which simplifies the construction of the device, facilitates its assembly and disassembly for replacement or field servicing, and reduces framing cost and size.

In scanner configurations where one of the analysis devices includes a generator, there typically, as known in the art, will be a top X-ray slit which is buttressed by a collimator housing assembly which also collimates the X-rays from the generator or by a detector housing assembly in which case the generator assembly is below the bed assembly such as bed assembly 126. Such an X-ray slit may be in the location of FIG. 3, X-ray slot 129. Embodiments of the invention can be used for hand carried parcel scanners screening items in size up to hand luggage, garment bags, backpacks, large brief cases, amorphous prison mattresses, etc., although the larger sizes may require more buttressing around slits or in the tunnel top corners, and thicker tunnel housing.

The analysis devices provided may include an explosive's vapour detector in the position of the detector 125 in the embodiment of FIG. 3. This vapour detector makes use of the relatively tight seal of air around the parcel scanned within the constricted size tunnel and lead X-Ray curtains on either end. Any side of the tunnel housing can be slitted and fitted with one of many types or makes of explosives' vapour detectors which suck in by air pump a sample of air and particulates, to analyze them for the presence of explosives, drugs or contraband, while the parcel is in the tunnel being X-Rayed. The vapour detector casing would have to be lead shielded for X-ray scatter. The preferred location to mount the vapor detector to maintain compactness would be above the enclosed area bounded by the tunnel housing and the top portion 126b of the bed assembly housing 126, preferably away from the line which bisects the tunnel housing, along which usually runs an X-ray fan slit upon which is mounted either the generator or a detector array. This is the location of detector 125 shown in FIG. 3. The area and dimensions of the vapour access slit would be determined by the internal air pump and hose attachment of the detector selected. Less compact arrangements could also be made out the tunnel sides. Venting through the bottom of the tunnel is also possible, but would be complicated by the placement of the moving conveyor belt.

We claim:

1. A scanner apparatus for scanning airport passenger luggage comprising:

a tunnel housing comprised of:
a top portion, and first and second side portions,
an entrance opening and an exit opening;

a bed assembly housing comprised of a top portion which together with the tunnel housing forms a substantially enclosed area, the bed assembly housing further comprising first and second side portions and wherein the first and second side portions of the tunnel housing are substantially fixed to the first and second side portions of the bed assembly housing, respectively;

an isolating device located at the entrance and exit openings of the tunnel housing;

a conveyor device for moving an object through the entrance opening of the tunnel housing and into the substantially enclosed area, subsequently through the substantially enclosed area, and thereafter out of the substantially enclosed area and out the exit opening of the tunnel housing, the conveyor device located substantially in the bed assembly housing; and an analysis device for analyzing objects within the substantially enclosed area of the tunnel housing;

said scanner occupying an amount of floor space; (new line, indent) means for minimizing the occupied floor space comprising having the top portion and the side portions of the tunnel housing each having a thickness of about 0.125 inches.

2. A scanner apparatus as recited in claim 1 wherein the analysis device is comprised of a detector array constructed of a substantially steel member which is used to connect the tunnel housing with the bed assembly housing.

3. A scanner apparatus comprising:

a tunnel housing comprised of:
a top portion, and first and second side portions,
an entrance opening and an exit opening;

a bed assembly housing comprised of a top portion which together with the tunnel housing forms a substantially enclosed area, an isolating device located at the entrance and exit openings of the tunnel housing;

a conveyor device for moving an object through the entrance opening of the tunnel housing and into the substantially enclosed area, subsequently through the substantially enclosed area, and thereafter out of the substantially enclosed area and out the exit opening of the tunnel housing, the conveyor device located substantially in the bed assembly housing; and an analysis device for analyzing objects within the substantially enclosed area of the tunnel housing; and wherein the tunnel housing further comprises:
a first slot in one of its portions near its entrance opening and
a second slot in one of its portions near its exit opening;

and wherein the isolating device comprises:
a first rod having a first curtain extending therefrom, wherein the first slot of the tunnel housing is adapted to receive the first curtain therein such that when the first curtain is inserted in the first slot, the first rod is mounted on the top portion of the tunnel housing and the first curtain extends through the first slot to substantially cover the entrance opening of the tunnel housing; and
a second rod having a second curtain extending therefrom, wherein the second slot of the tunnel housing is is adapted to receive the second curtain therein such that when the second curtain is inserted in the second slot, the second rod is mounted on the top portion of the tunnel housing and the second curtain extends through the second slot to substantially cover the exit opening of the tunnel housing.

4. A method for scanning airport passenger luggage objects comprising the steps of:
providing a tunnel housing comprised of:
a top portion, and first and second side portions,
an entrance opening and an exit opening;
providing a bed assembly housing comprised of a top portion which together with the tunnel housing form a substantially enclosed area,
providing the bed assembly housing so that the bed assembly housing also has first and second side portions;
fixing the first and second side portions of the bed assembly housing to the first and second side portions of the tunnel housing, respectively.
locating an isolating device at the entrance and exit openings of the tunnel housing;
locating a conveyor device substantially in the bed assembly housing, the conveyor device used for moving an object through the entrance opening of the tunnel housing and into the substantially enclosed area, subsequently through the substantially enclosed area, and thereafter out of the substantially enclosed area and out the exit opening of the tunnel housing; and
providing an analysis device for analyzing objects within the substantially enclosed area of the tunnel housing;
said scanning conducted by a scanner occupying an amount of floor space;
minimizing the occupied floor space by having the top portion and the side portions of the tunnel housing each having a thickness of about 0.125 inches.

5. A method for constructing a scanner for scanning objects as recited in claim 4, wherein
each of the top portion, and first and second side portions of the tunnel housing
has a thickness of about 0.125 inches.

6. A method scanning airport passenger luggage objects comprising the steps of:
providing a tunnel housing comprised of: a top portion, and first and second side portions,
an entrance opening and an exit opening;
providing a bed assembly housing comprised of a top portion which together with the tunnel housing form a substantially enclosed area;
locating an isolating device at the entrance and exit openings of the tunnel housing;
locating a conveyor device substantially in the bed assembly housing, the conveyor device used for moving an object through the entrance opening of the tunnel housing and into the substantially enclosed area, subsequently through the substantially enclosed area, and thereafter out of the substantially enclosed area and out the exit opening of the tunnel housing; and
providing an analysis device for analyzing objects within the substantially enclosed area of the tunnel housing, and
using the analysis device to connect the tunnel housing with the bed assembly housing;
said scanning conducted by a scanner occupying an amount of floor space;
minimizing the occupied floor space by having the top portion and the side portions of the tunnel housing each having a thickness of about 0.125 inches.

7. A method for constructing a scanner for scanning objects comprising the steps of:
constructing a tunnel housing comprised of:
a top portion, and first and second side portions, and an entrance opening and an exit opening;
constructing a bed assembly housing comprised of a top portion which together with the tunnel housing form a substantially enclosed area;
locating an isolating device at the entrance and exit openings of the tunnel housing;
locating a conveyor device substantially in the bed assembly housing, the conveyor device used for moving an object through the entrance opening of the tunnel housing and into the substantially enclosed area, subsequently through the substantially enclosed area, and thereafter out of the substantially enclosed area and out the exit opening of the tunnel housing; and
constructing an analysis device for analyzing objects within the substantially enclosed area of the tunnel housing;
providing a first slot in one of the portions of the tunnel housing near its entrance opening and
providing a second slot in one of the portions of the tunnel housing near its exit opening;
and wherein the step of locating the isolating device comprises:
inserting a first rod having a first curtain extending from it, through the first slot,
substantially fixing the first rod to a portion of the tunnel housing near the entrance opening of the tunnel housing;
inserting a second rod having a second curtain extending from it, through the second slot, and
substantially fixing the second rod to a portion of the tunnel housing near the exit opening of the tunnel housing.

* * * * *